United States Patent [19]

Willingham

[11] Patent Number: 5,145,981
[45] Date of Patent: Sep. 8, 1992

[54] USE OF ANTIMONY SALT STABILIZERS FOR 3-ISOTHIAZOLONES

[75] Inventor: Gary L. Willingham, Glenside, Pa.
[73] Assignee: Rohm and Haas, Philadelphia, Pa.
[21] Appl. No.: 625,279
[22] Filed: Dec. 10, 1990
[51] Int. Cl.$^5$ ............................................. A01N 43/80
[52] U.S. Cl. ..................................................... 548/213
[58] Field of Search .......................................... 548/213

[56] References Cited

U.S. PATENT DOCUMENTS

| | | | |
|---|---|---|---|
| 3,523,121 | 8/1970 | Lewis et al. | 548/213 |
| 3,761,488 | 9/1973 | Lewis et al. | 548/213 |
| 3,870,795 | 3/1975 | Miller et al. | 548/213 |
| 4,067,878 | 1/1978 | Miller et al. | 548/243 |
| 4,127,687 | 11/1978 | Dupont | 428/35 |
| 4,129,274 | 12/1978 | Greenfield et. al. | 548/213 |
| 4,150,026 | 4/1979 | Miller et al. | 548/213 |
| 4,165,318 | 8/1979 | Greenfield | 548/213 |
| 4,241,214 | 12/1980 | Miller et al. | 548/213 |
| 4,783,221 | 11/1988 | Grove | 106/18.22 |
| 4,906,274 | 3/1990 | Mattox | 548/213 |

OTHER PUBLICATIONS

Kathon ® MW Microbiocide and Kathon ® 893 MW Fungicide: Analysis in Metal Working Fluids by High Performance Liquid Chromatography 1988 (Rohm and Haas Company).

*Primary Examiner*—Robert Gerstl
*Attorney, Agent, or Firm*—Michael B. Fein

[57] ABSTRACT

Composition comprising (A) 3-isothiazolone biocide compound and (B) an amount of a second compound selected from the group consisting of antimony salts to stabilize said 3-isothiazolone and method of stabilizing the 3-isothiazolones comprising combining with the antimony salts are disclosed.

12 Claims, No Drawings

USE OF ANTIMONY SALT STABILIZERS FOR 3-ISOTHIAZOLONES

BACKGROUND OF THE INVENTION

1. Field of the Invention

This invention concerns the stabilization of 3-isothiazolone compounds by the incorporation with those compounds of certain antimony salt compounds.

2. Description of the Prior Art

Isothiazolones have generated high commercial interest as microbicides to prevent spoilage of certain aqueous and non-aqueous products caused by microorganisms. Isothiazolones are highly effective microbicides (as used herein, "microbicides" includes bactericides, fungicides and algicides and microbicidal activity is intended to include both the elimination of and the inhibition or prevention of growth of microbial organisms such as bacteria, fungi and algae); by suitable choice of functional groups, they are useful in a broad range of applications. However, it has been long recognized that either in storage prior to addition to the substrate to be treated or after addition, their efficacy may be decreased because they are not stable under practical conditions of long-term storage. Means have thus been sought for some time to improve the stability of isothiazolones.

U.S. Pat. Nos. 3,870,795 and 4,067,878 teach the stabilization of isothiazolones against chemical decomposition by addition of a metal nitrite or metal nitrate, but teach that other common metal salts, including carbonates, sulfates, chlorates, perchlorates, and chlorides are ineffective in stabilizing solutions of isothiazolones, such solutions usually being in water or in an hydroxylic solvent.

U.S. Pat. Nos. 4,150,026 and 4,241,214 teach that metal salt complexes of isothiazolones are useful because they have enhanced thermal stability, while retaining biological activity.

It is known to use certain organic stabilizers for isothiazolones, generally for use situations where metal salts may create problems, such as corrosion, coagulation of latices, insolubility in non-aqueous media, interaction with the substrate to be stabilized, and the like. Formaldehyde or formaldehyde-releasing chemicals are known as stabilizers, (see U.S. Pat. Nos. 4,165,318 and 4,129,448), as are certain organic chemicals such as orthoesters (U.S. Pat. No. 4,906,274) and epoxides (U.S. application. Ser. No. 194,234).

In certain applications, however, it is desirable to avoid addition of organic stabilizers by virtue of their volatility, decomposition under high heat, higher cost, difficulty in handling, potential toxicity, and the like. Formaldehyde is a suspected carcinogen, and it is desirable not to use formaldehyde in applications where contact with human skin or lungs may occur.

In actual use, copper salts, such as copper sulfate, have proved efficacious in the stabilization of isothiazolones. However, copper salts may be undesirable in effluent streams in such operations as in the manufacture of stabilized isothiazolones or in their blending into a product or the use of that product. Copper salts, especially the chlorides, may contribute to possible corrosion, or in the presence of polymers in aqueous dispersion may lead to coagulation of the dispersion.

SUMMARY OF THE INVENTION

It is an object of the invention to provide a stabilization system for isothiazolones which overcomes some or all of the disadvantages of prior art systems. It is also an object to provide an isothiazolone stabilized by only low levels of stabilizer so as to avoid interference with other components in systems in which isothiazolones are used as microbicides.

These objects, and others which will become apparent from the following disclosure, are achieved by the present invention. It has been surprisingly found that isothiazolones may be stabilized against decomposition by the addition of an antimony salt compound to the composition containing the isothiazolone. Accordingly the invention provides in one aspect a composition comprising:

(A) at least one 3-isothiazolone of the formula (I)

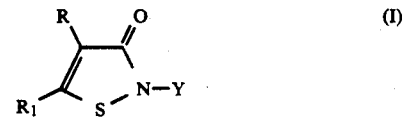

wherein

Y is an unsubstituted or substituted $(C_1-C_{18})$ alkyl, an unsubstituted or substituted $(C_3-C_{12})$ cycloalkyl, an unsubstituted or halogen-substituted $(C_2-C_8)$ alkenyl or alkynyl, an unsubstituted or substituted $(C_7-C_{10})$ aralkyl, or an unsubstituted or substituted aryl; and R and $R^1$ is each independently H, halogen or $(C_1-C_4)$ alkyl; and (B) an amount of a second compound selected from the group consisting of antimony salts to stabilize said 3-isothiazolone.

In another aspect, the invention comprises a method for inhibiting or preventing the growth of bacteria, fungi, yeast or algae in a locus subject or susceptible to contamination by bacteria, fungi, yeast or algae, which comprises incorporating onto or into the locus, in an amount which is effective to adversely affect the growth of bacteria, fungi, yeast, or algae, the aforementioned composition.

DETAILED DESCRIPTION OF THE INVENTION AND THE PREFERRED EMBODIMENTS

The isothiazolones which are stabilized include those disclosed in U.S. Pat. Nos. 3,523,121 and 3,761,488 and represented by the formula

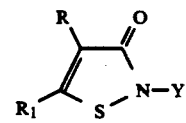

as defined above. In particular Y may be a $(C_1-C_{18})$alkyl or $(C_3-C_{12})$cycloalkyl each optionally substituted with one or more of hydroxy, halo, cyano, alkylamino, dialkylamino, arylamino, carboxy, carbalkoxy, alkoxy, aryloxy, alkylthio, arylthio, haloalkoxy, cycloalkylamino, carbamoxy, or isothiazolonyl; and unsubstituted or halo-substituted $(C_2-C_8)$ alkenyl or alkynyl; a $(C_7-C_{10})$ aralkyl optionally substituted with one or more of halogen, $(C_1-C_4)$alkyl or $(C_1-C_4)$alkoxy; and an aryl optionally substituted with one or more of halogen, nitro, $(C_1-C_4)$alkyl, $(C_1-C_4)$alkyl-acylamino, carb$(C_1-C_4)$alkoxy or sulfamyl.

Preferred substituents for Y are substituted or unsubstituted $(C_1-C_{18})$ alkyl or $(C_3-C_{12})$cycloalkyl; R is preferred to be H, methyl or Cl; and $R^1$ is preferred to be H or Cl. Representative of such preferred Y substituents are methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl, hydrogen, and the like.

Particularly preferred isothiazolones are 5-chloro-2-methyl-3-isothiazolone, 2-methyl-3-isothiazolone, 2-n-octyl-3-isothiazolone, 4,5-dichloro-2-cyclohexyl-3-isothiazolone and 4,5-dichloro-2-octyl-3-isothiazolone.

Most preferred is 5-chloro-2-methyl-3-isothiazolone, either as a sole compound or in admixture with 2-methyl-3-isothiazolone. When in admixture, the preferred ratio of monochlorinated/unchlorinated isothiazolone is from about 70:30 to about 85:15, and an especially preferred ratio is from about 70:30 to about 80:20. A second especially preferred isothiazolone is 2-methyl-3-isothiazolone in combination with low levels of 5-chloro-2-methyl-3-isothiazolone, a preferred ratio being from about 98:2 to about 96:4, and an especially preferred ratio being about 97:3.

Preferred antimony salts are antimony sulfate and antimony pentoxide.

Generally, the composition of the invention will be in the form of a solution. Typical formulation ranges are illustrated in the following Table (all percentages are parts by weight) for both a concentrated solution of the isothiazolone and a dilute solution. For certain uses, such as shipping of large quantities, more concentrated solutions may also be utilized.

| FORMULATIONS TABLE | | |
|---|---|---|
| Isothiazolone | Antimony salt | Solvent |
| (I, Supra) | | |
| 0.01-99.9999% | 0.0001-99.9% | 0-99.9899% |
| Preferred | | |
| 0.1-50% | 0.01-20% | 30-99,89% |

Solvents may be used to dissolve the isothiazolones and may be any organic solvent which dissolves the isothiazolones, is compatible with the proposed end use, does not destabilize the isothiazolone, and does not react with the antimony salt to eliminate its stabilizing action.

Hydroxylic solvents, for example, polyols, such as glycols, alcohols and the like, may be used. Under conditions of high dilution and high ratios of stabilizer to isothiazolone, glycols may be successfully used. In certain formulations, hydrocarbons, either aliphatic or aromatic, are useful solvents.

Preferred solvents are capped polyols, wherein the free hydroxyl group is replaced with an ether or ester function. Especially preferred are 2,5,8,11-tetraoxadodecane, commonly known as triethylene glycol dimethyl ether, and 4,7-dioxaundecanol-1acetate, commonly known as diethylene glycol butyl ether acetate.

Water is a solvent for certain of the preferred isothiazolones and the antimony salt may be employed in aqueous formulations.

The amounts of antimony salt employed will vary depending on use conditions and concentrations of the isothiazolone in the mixture: effective amounts of antimony salt based on isothiazolone may be ratios in the range of from about 1:100 to about 1000:1 stabilizer to isothiazolone. In concentrated solutions, ratios are generally from about 1:50 to about 50:1. Obviously higher amounts may be used, but at additional cost. At high levels of dilution of the isothiazolone (such as from 1 to 10,000 ppm isothiazolone in the solvent), the ratio of stabilizer to isothiazolone can range from about 1:10 to about 20:1. The preferred range is from 1:1 to 20:1. The amount of antimony salt must be sufficient to stabilize the 3-isothiazolone against chemical degradation.

The stabilization advantages of the antimony salts of the present invention are noted even when the isothiazolone contains other salt stabilizers recorded in U.S. Pat. Nos. 3,870,795, 4,067,878, 4,150,026 and 4,241,214.

Uses of these new antimony salt stabilized microbicides are typically at any locus subject to contamination by bacteria, fungi, yeast or algae. Typically loci are in aqueous systems such as water cooling, laundry rinse water, oil systems such as cutting oils, oils fields and the like where microorganisms need to be killed or where their growth needs to be controlled. However these stabilized microbicides may also be used in all applications for which known microbicidal compositions are useful; preferred utilities of the compositions are to protect wood, paint, adhesive, glue, paper, textile, leather, plastics, cardboard, lubricants, cosmetics, metla working fluids, food, caulking, feed and industrial cooling water from microorganisms.

The following lists typical industries and applications of compositions:

| Industry | Application |
|---|---|
| Adhesives, sealants | adhesives |
| | caulks |
| | sealants |
| Agriculture/food chain | adjuvant preservation |
| | agricultural active ingredient |
| | agricultural chemical preservation |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated household products | fabric softeners |
| | polishes |
| | waxes |
| | hand dish detergents |
| | raw materials |
| | liquid detergents |
| | hand soaps |

-continued

| Industry | Application |
|---|---|
| Industrial processing, misc | electrodeposition paint, baths, rinses. |
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry rinse water |
| | sanitizers-laundry |
| Leather, leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings | emulsions |
| | paints |
| Paper and wood pulp, their products | absorbant materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products, storage, transportation and production |
| | recycled petroleum products |
| | residual fuel oils |
| | turbine oils |
| Photographic Chemicals and process | photographic processing - wash water, rinses |
| | photoprocessing |
| | photoplate processing chemicals (developers, stabilizer etc) |
| Printing | fountain solutions (printing) |
| | ink components (pigments, resins, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemicals |
| | enzymes-food production |
| | enzymes |
| | enzymes-industrial |
| | gel cushions |
| | marine antifoulants |
| | mildewcides |
| | wood |

| Industry | Application |
|---|---|
| | plastics |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

Because isothiazolones are so active as microbicides and only low levels of antimony salts are required to achieve stabilization, the amount of antimony salt in systems being treated will be very small, and therefore it is not likely to interfere with other components in systems requiring protection or with systems to which the protected systems will be applied. Potential areas of general application include metal-working fluids, cooling water, and air washers.

One significant area of application for the compositions of the invention is as microbicides in metal working fluids. Metal working fluids are proprietary combinations of chemicals, which may contain, inter alia, ingredients such as alkanolamines, petroleum sulfonate surfactants, oils (naphthenic, paraffinic, etc.), chlorinated paraffins and fatty esters, sulfurized fatty compounds, phosphate esters, fatty acids and their amine salts, glycols, polyglycols, boric acid esters and amides. They are utilized in the milling, machining, drilling, and other processing technologies for fabricating metal for the purposes of lubricating, cooling, preventing surface corrosion, and the like. They are sold in the form of active metal working fluids (MWF) concentrate, and are diluted in use to 1–10% active ingredients in water.

Because metal working fluids are recycled and stored, the growth of microorganisms is favored. Isothiazolones have been found effective in preventing the growth of such organisms. Certain of the components in the metal working fluids will tend to destroy the isothiazolone and so remove its microbicidal protective activity, so that stabilizers for the isothiazolone against such degradation are desirable.

It is known in the art that the performance of microbicides may be enhanced by combination with one or more other microbicides. Thus, other known microbicides may be combined advantageously with the composition of this invention.

The following examples are intended to illustrate the present invention and not to limit it except as it is limited by the claims. All percentages are by weight unless otherwise specified, and all reagents are of good commercial quality unless otherwise specified. Methods for quantitative determination of the isothiazolones in the following examples in metal-working fluids are described in detail in "Kathon® 886 MW Microbicide and Kathon® 893 MW Fungicide: Analysis in Metalworking Fluids by High-Performance Liquid Chromatography", 1988, Rohm and Haas Company.

EXAMPLES

EXAMPLES 1 TO 4

These examples demonstrate the stabilizing effect of antimony salts for isothiazolones added to metal working fluids (MWF). MWF concentrates A-D were a "semi-synthetic" type having about 10 to 15 percent naphthenic/paraffinic oil, about 50 percent water, emulsifying agents, pH adjusting amines, anticorrosive agents, and EP (extreme pressure) agents.

Into a glass vial in the following order were placed: a) 5 parts by weight of the MWF concentrate solution, b) 5 parts of the stabilizer in solution or dispersion, c) 5 parts water, d) 5 parts of an aqueous solution containing 80 ppm active ingredient (AI), prepared by dilution of a 14.4% aqueous solution of an approximately 75/25 mixture of 5-chloro-2-methyl-3-isothiazolone and 2-methyl-3-isothiazolone, the former being considered the active ingredient for these purposes; also present was 9.2 weight percent magnesium chloride and 15.7% magnesium nitrate. Thus the final mixture contained 3–5% of the MWF concentrate, 15 ppm active ingredient of the isothiazolone, and 0 (control) to 1,000 ppm of the stabilizer.

The vials were then capped, stored at ambient room temperature in a closed cabinet for a designated time, filtered through a 0.45 micron filter into another vial and analyzed the same day. The relative concentration of the active ingredient was determined by reverse phase high pressure liquid chromatography, utilizing a Varian model 5500 chromatograph and an ultraviolet detector.

TABLE 1

STABILIZATION OF 5-CHLORO-2-methyl-3-isothiazolone IN MWF CONCENTRATE A AFTER FOUR DAYS
Original system contained 15 ppm 5-chloro-2-methyl-3-isothiazolone (AI) with 3% MWF Concentrate A in water.
All stabilizers were added at 1000 ppm.

| Stabilizer | % AI remaining |
|---|---|
| None | <1 |
| Sodium antimony tartrate | 11 |
| Potassium antimony tartrate | 12 |
| Antimony pentoxide | 17 |
| Antimony sulfate | 40 |

TABLE 2

MWF A AND B STABILIZED WITH POTASSIUM ANTIMONY TARTRATE AGED 3 DAYS
Original system contained 15 ppm 5-chloro-2-methyl-3-isothiazolone (AI) with 3% MWF concentrate A in water.
Stabilizer was added at 100 ppm of antimony cation.

| | % AI remaining | |
|---|---|---|
| Stabilizer | MWF A | MWF B |
| None | 43 | <1 |
| Potassium antimony tartrate | 49 | 25 |

TABLE 3

MWF C AND D STABILIZED WITH POTASSIUM ANTIMONY TARTRATE AGED 3 AND 10 DAYS
Original system contained 15 ppm 5-chloro-2-methyl-3-isothiazolone (AI) with 3% MWF concentrate C or D in water.

| Stabilizer | Stabilizer level (ppm antimony) | % AI remaining | | | |
|---|---|---|---|---|---|
| | | MWF-C | | MWF D | |
| | | 3 days | 10 days | 3 days | 10 days |
| None | 0 | 56 | 33 | 8 | <1 |
| Potassium antimony tartrate | 20 | 51 | 30 | 53 | 17 |
| Potassium antimony tartrate | 200 | 65 | 52 | 39 | 19 |

TABLE 4

MWF A STABILIZED WITH ANTIMONY SULFATE AT 1000 PPM AGED 5 DAYS
Original system contained 18 ppm 5-chloro-2-methyl-3-isothiazolone (AI) with 3% MWF concentrate in water

| Stabilizer | % AI remaining |
|---|---|
| None | <1 |
| Antimony sulfate | 64 |

While the invention has been described with reference to specific examples and applications, other modifications and uses for the invention will be apparent to those skilled in the art without departing from the spirit and scope of the invention defined in the appended claims.

I claim:

1. A method of stabilizing a 3-isothiazolone antimicrobial compound against chemical degradation in antagonistic environments comprising combining with said 3-isothiazolone compound an amount of a second compound selected from the group consisting of antimony salts sufficient to stabilize said 3-isothiazolone compound.

2. A method according to claim 1 wherein said antimony salt is combined in a weight ratio to 3-isothiazolone of about 1:10 to 100:1.

3. A method according to claim 1 wherein said ratio is about 1:1 to 20:1.

4. A method according to claim 1 wherein said environment is selected from the group consisting of metal working fluid, latex paint, bulk latex, cosmetics, cooling towers, and surfactants.

5. A method according to claim 1 wherein said antimony salt is selected from the group consisting of antimony sulfate, potassium antimony tartrate, sodium antimony tartrate, and antimony pentoxide.

6. A composition comprising 3-isothiazolone biocide compound and an amount of a second compound selected from the group consisting of antimony sulfate, potassium antimony tartrate, sodium antimony tartrate, and antimony pentoxide sufficient stabilize said 3-isothiazolone.

7. A composition according to claim 6 further including a composition antagonistic to said 3-isothiazolone selected from the group consisting of metal working fluid, latex paint, bulk latex, cosmetic, cooling tower water, and surfactant.

8. A composition according to claim 6 wherein the weight ratio of (B) to (A) is about 1:10 to 100:1.

9. A composition according to claim 8 wherein said ratio is about 1:1 to 20:1.

10. A composition according to claim 6 wherein said 3-isothiazolone is of the formula (I)

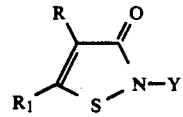

wherein

Y is an unsubstituted or substituted $(C_1-C_8)$ alkyl, an unsubstituted or substituted $(C_3-C_{12})$ cycloalkyl, an unsubstituted or halogen-substituted $(C_2-C_8)$ alkenyl or alkynyl, an unsubstituted or substituted $(C_7-C_{10})$ aralkyl, or an unsubstituted or substituted aryl; and R and $R^1$ is each independently H, halogen or $(C_1-C_4)$ alkyl.

11. A composition according to claim 6 wherein Y is selected from: $(C_1-C_8)$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylethio, arylthio, haloalkoxy, cycloalkylamino, carbamoxy, or isothiazolonyl; an unsubstituted or halo-substituted $(C_2-C_8)$ alkenyl or alkynyl; a $(C_7-C_{10})$aralkyl optionally substituted with one or more of halogen, $(C_1-C_4)$alkyl or $(C_1-C_4)$alkoxy; and an optionally substituted with one or more of halogen, nitro, $(C_1-C_4)$alkylacylamino, carb$(C_1-C_4)$alkoxy or sulfamyl.

12. A composition according to claim 6 which additionally comprises a polyol solvent.

* * * * *